United States Patent [19]

Jones

[11] Patent Number: 5,059,209
[45] Date of Patent: Oct. 22, 1991

[54] COMPOSITE MATERIALS FOR ORTHOPAEDICS

[75] Inventor: Michael E. B. Jones, Chester, England

[73] Assignee: Imperial Chemical Industries PLC, London, England

[21] Appl. No.: 342,810

[22] Filed: Apr. 25, 1989

[30] Foreign Application Priority Data

Apr. 26, 1988 [GB] United Kingdom ................. 8809863

[51] Int. Cl.⁵ ........................... A61F 2/36; A61F 2/28
[52] U.S. Cl. ......................................... 623/23; 623/16
[58] Field of Search .................................. 623/16, 66; 523/113–117

[56] References Cited

U.S. PATENT DOCUMENTS

| | | | |
|---|---|---|---|
| 4,131,597 | 12/1978 | Bluethgen et al. | 260/42.18 |
| 4,381,918 | 5/1983 | Ehrnford | 433/199 |
| 4,714,721 | 12/1987 | Franek et al. | 523/117 X |
| 4,790,851 | 12/1988 | Suire et al. | 623/16 |

FOREIGN PATENT DOCUMENTS

| | | |
|---|---|---|
| 0013491 | 7/1980 | European Pat. Off. . |
| 0059649 | 9/1982 | European Pat. Off. . |
| 0112650 | 7/1984 | European Pat. Off. . |
| 0162651 | 11/1985 | European Pat. Off. . |
| 1465897 | 3/1977 | United Kingdom . |
| 2085461 | 4/1982 | United Kingdom . |

*Primary Examiner*—Alan W. Cannon
*Attorney, Agent, or Firm*—Cushman, Darby & Cushman

[57] ABSTRACT

A prosthetic device prepared by curing an intimate mixture of an addition-polymerizable composition and a particulate inorganic solid which provides up to 80% by volume of the prosthetic device. The prosthetic device has a flexural modulus similar to the boney tissue which it contacts in use.

20 Claims, 1 Drawing Sheet

COMPOSITE MATERIALS FOR ORTHOPAEDICS

The present invention relates to composite materials for use in orthopaedics, to processes for preparing the composite materials, to prosthetic devices (i.e. shaped products adapted for location and use within the body) incorporating them, and particularly to so-called endoprosthesis, i.e. to the artificial replacement of parts of the anatomy internally resident in the human or animal body, principally bone.

Many endoprosthetic devices are known to the skilled man. As examples of such devices may be mentioned inter alia so-called "bone plates" which are used to hold fractured bones in alignment during healing; plates or inserts used to cover damage to a bone or to replace damaged or destroyed bone or to reinforce it, for example in the skull or long bones; and components of replacement joints, particularly the hip and knee joints, although the invention is not limited to such devices. Such devices must be of a shape, configuration and properties appropriate to their proposed application. Preferably, such that they are acceptable to the living tissue with which they are likely to come into contact when in use for a time sufficient for them to perform their intended function without unacceptable damage or undue discomfort to the recipient. More preferably, they are sufficiently acceptable for a period such that where appropriate they need not be removed from the body during the life of the recipient.

Animal bone and ivory have, in the past, been employed in orthopaedic prosthesis. As with all natural materials, however, it is difficult to ensure the supply of these materials with adequate and predictable properties. Moreover, they contain protein which is not of the patient's origin and this biological incompatibility often initiates an adverse response from the body tissue with which they are in contact. For example, inflammatory reactions or rejection may arise. Accordingly, surgeons have resorted and still resort, to a variety of synthetic engineering materials, the envisaged uses of which materials were often remote from prosthesis.

For example, in total hip replacement: often, the femoral head is replaced with a cast alloy, typically an austenitic stainless steel or Co-Cr alloy. The aforesaid cast alloy is secured, typically by a polymethylmethacrylate bone cement, and is seated in a high molecular weight, high density polyethylene acetabular cup. The alloys used are selected primarily by virtue of their resistance to corrosion, adequate fracture toughness, creep and fatigue strength. They have proved satisfactory but less than ideal, in such applications; as a result, attention has recently been devoted to the development of even more "bioinert" prosthetic materials with comparable strength properties. Examples of such bioinert prosthetic materials include titanium alloys and ceramics, principally alumina. The brittle nature of ceramics, however, presents further problems for prosthesis. Further, materials such as plastics and composite materials comprising for example a long fibre-reinforced polymer material, eg carbon-fibre-filled thermoplastics, have been suggested for use in prosthetic devices. All such materials have been found to have disadvantages. For example, metal and ceramic devices tend to have too high a modulus so that the adjacent bone tends to regress during extended periods of use, resulting in loosening of the device. Devices comprising fibre-reinforced composites sometimes initiate a tissue reaction. Such tissue reaction may be a response to the chemical nature of the matrix of the composite or may result from the presence of fine particles of the fibrous component of the device, resulting possibly from wear and/or abrasion of the fibre where it is present at or adjacent the surface of the device. Where carbon fibre is used as fibrous reinforcement in a prosthetic device which is disposed near certain surfaces of the human body, eg the face, the inherent black colour of such devices often leads to cosmetic problems.

We have now devised a composite material for use in prosthetic devices which overcomes many of the aforesaid deficiencies. Furthermore, it has a flexural modulus similar to the boney tissue which it contacts in use. It is believed that such similarity alleviates the problems associated with the loosening of implants and thus extends their useful working life.

According to the present invention there is provided a prosthetic device comprising a composite characterised in that the composite is preparable by curing a composition (hereinafter referred to for convenience as Composition A) which comprises an intimate mixture of Component A: an addition-polymerisable composition; and Component B: at least one particulate inorganic solid which provides up to about 80% by volume of the composite.

It will be appreciated that the prosthetic device will be chosen such that the shape, configuration and chemical properties thereof are appropriate to the proposed location and disposition thereof within the living body. In a preferred aspect, the present invention provides a femural stem (hip joint) prosthetic device.

According to a further aspect of the present invention there is provided a composition (Composition A) as hereinbefore defined.

Composition A may be in the form of an intimate admixture, a dispersion or suspension (which terms are used interchangeably herein) of the particulate inorganic solid (Component B) in the addition-polymerisable composition (Component A).

The composite of which the prosthetic device according to the present invention is comprised has low water extractibles, preferably less than 0.15%; has low water uptake, preferably less than 0.3%; and preferably it can be autoclaved with no undue detrimental affect.

"Water extractibles" and "water-uptake" are defined hereinafter.

Component A when cured gives a product which (a) has a flexural modulus of about 3 GPa; (b) has a flexural strength and modulus which remain substantially unchanged when autoclaved in steam at about 120° C. for about 20 minutes; and (c) remains substantially visually unchanged when saturated with water at 74° C.

Component A bears on average more than one addition- polymerisable olefinically unsaturated carbon-carbon double bond per molecule. It is often preferred that it comprises a plurality of such carbon-carbon double bonds. Component A which may be neat or an admixture, will be chosen (a) in the light of (i) the processability properties required in Composition A, (ii) the properties of the prosthetic device according to the present invention and (b) such that the Composition A containing the appropriate amount of filler does not shrink unduly on curing.

As examples of addition-polymerisable compositions bearing a plurality of addition-polymerisable carbon-carbon double bonds may be mentioned inter alia monomers, e.g. (i) triethylene glycol dimethacrylate, or (ii)

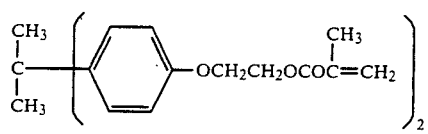

or preferably oligomers.

As examples of oligomers may be mentioned inter alia unsaturated aromatic-compound/aldehyde oligomers, e.g. as described in our European Patent Specification Nos. 0,112,650A and 0,162,651A.

As examples of addition-polymerisable compositions bearing one addition-polymerisable carbon-carbon double bond may be mentioned inter alia monomers, for exampled alkyl (alk)acrylates, e.g. methyl methacrylate; cyclohexyl methacrylate; or 2, 3, 4, 5, 6-pentafluorostyrene.

The presence of a monomer in Composition A often reduces the viscosity thereof and allows certain properties, e.g. water-uptake, of the prosthetic device prepared therefrom to be adjusted. Where the monomer contains one carbon-carbon double bond it reduces the cross-link density of the composite and hence tends to improve the mechanical properties of the device.

The viscosity of Component A is, or is adapted, such that sufficient of the inorganic particles may be mixed therewith such that on curing Composition A, a composite which has the flexural modulus herein described is obtained.

The particulate inorganic solid is stiff enough to impart desired rigidity to the device and is substantially non-leachable, i.e. stable for extended periods, e.g. more than 10 years, in a moist environment.

As examples of suitable particulate inorganic solids which may be used as, or in, Component B may be mentioned inter alia hydroxy apatite, talc, mica, alumina, silica or preferably a glass, eg a borosilicate or a Raysorb (RTM), or more preferably a radio-opaque material, for example a glass, eg Raysorb T3000 (RTM).

We do not exclude the possibility that a portion, up to 10% say, of the particulate inorganic solid may be in the form of, for example, plates or fibrils.

Preferably, the particulate inorganic solid may be treated with a suitable coupling agent to improve the bonding thereof to the polymerisable component. For example, where the particulate inorganic solid is silica it may be treated with a suitable silane coupling agent, e.g. $\gamma$-methacrylyl-oxypropyl-trimethoxysilane.

Often a stabiliser or dispersing agent, e.g. a long chain amine or phosphate (as is more fully described in our European Patent Specification No 0, 013, 491) is used in Composition A. This use tends to improve the stability of the dispersion of Component B in Component A and to facilitate the shaping of Composition A in a mould.

It will be appreciated that the volume % of the particulate inorganic solid in Composition A will depend on inter alia the size, shape and size distribution of the particles, and the efficacy of dispersion of the particles in Component A. These will be chosen such that Composition A has sufficient mobility to allow the shaping/fabrication thereof to be carried out and the composite to have the desired modulus. The lower limit of the volume % of the particulate inorganic solid will be readily determined by the skilled man by simple experiment.

Composition A preferably comprises 10–80%, more preferably 40–75% and particularly more preferably 65–70% by volume of a particulate inorganic solid. Above about 80% v/v, it is found that the particulate inorganic solid often cannot be distributed homogeneously in Composition A. Below about 50% v/v. prosthetic devices prepared by polymerisation of the composition tend to be too compliant. The particulate inorganic solid tends both to reinforce the composite and to enhance its stiffness.

The particulate inorganic solid may be used in the form of ground particles, preferably wherein the particle size is from 90% thereof being less than 100 $\mu$m to 1.0 $\mu$m, preferably from 90% being less than 50 $\mu$m to 0.1 $\mu$m. Preferably a portion of the particles are sub-micron particles, more preferably about 10% thereof are such particles, eg of silica. The use of such sub-micron particles tends to facilitate the obtaining of a high volume % particle content. Mixtures of differing particulate inorganic solids often further facilitate the obtaining of a high volume % particle content.

The particulate inorganic solid may also be used in the form of acicular particles or platelets, the latter preferably having a maximum length of 500 $\mu$m and a maximum thickness of 20 $\mu$m.

The composites prepared by polymerisation of Composition A have a flexural modulus in the range of values recorded for compact bone, preferably between 15 and 30 GPa, more preferably about 20 GPa.

As examples of uses for prosthetic devices according to the present invention may be mentioned inter alia facial reconstruction, dental implants, fracture repair, and artificial joints. For example, it may be used as the direct engagement of bone which may be a fracture fixation device, a jaw prosthesis or a prosthesis for the simple substitution of a local section of bone; especially, however, the endoprosthesis is a bone joint device, particularly for partial or total replacement of the hip or knee joints. In particular, the composite may be used to fabricate either or both of the femural head and stem and the acetabular cup into which the head seats in vivo, although it may be used in the prosthesis of any joint affected by arthrosis.

We do not exclude the possibility that the device may be reinforced by incorporation of a suitable fibre, e.g. glass, in the composite.

It will be appreciated that the prosthetic device should be biocompatible, i.e. the addition-polymerisable composition, the cured product prepared therefrom, the particulate inorganic filler and a fibre, where present, should be substantially non-toxic to mammals, particularly humans, and that minimal amounts, less than 0.2% say, of water extractables should be extractable therefrom on exposure to water at 74° C. until saturated.

It is often preferred that a portion, and often the whole, of the wear surface, i.e. the portion of the head in contact with the cup where the device is a femural head replacement, of the prosthetic device is coated with a wear resistant coating. As examples of such coatings may be mentioned inter alia ceramics, suitable metals, eg steel, and thermoplastics.

The thickness of the aforesaid coating will be chosen such that it is effective in reducing wear of the prosthetic device. It will be appreciated that the thickness will be chosen in the light of inter alia the location and period of use of the prosthetic device.

Adhesion of the coating to the prosthetic device may be by the natural adhesive properties of the coating and the composite, use of an appropriate adhesive, by mechanical keying of the coating into the device or by combinations of these. For example, where the prosthetic device is a femural head and the wear-resistant surface is a thermoplastic or metal the surface may be provided by a portion of the mould in which Composition A is cured to produce the device.

The invention is illustrated by the following drawings which show, by way of example only, three embodiments of the present invention.

In the Drawings

Figure 1:
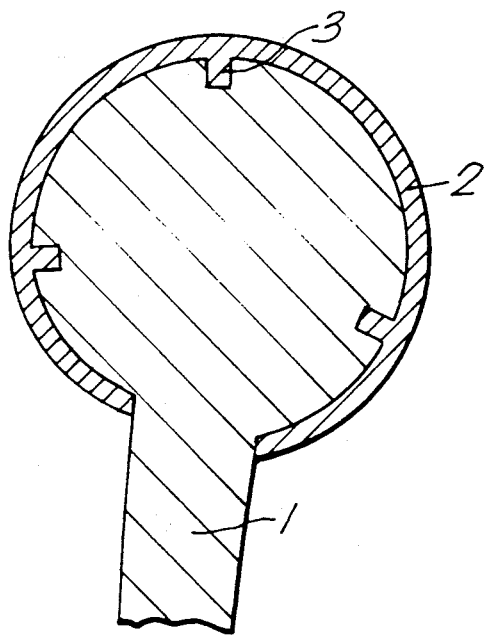
FIG. 1 is a sectional view of a portion of a femural head bearing a wear-resistant coating.

In FIG. 1, a femural head 1 according to the present invention is provided with a metal alloy coating 2 eg Vitalium (RTM) which is formed with a plurality of keys 3. In the preparation of the head, the coating 2 was a portion of the mould in which Composition A was cured. On curing, the keys 3 became trapped in the head.

Figure 2:
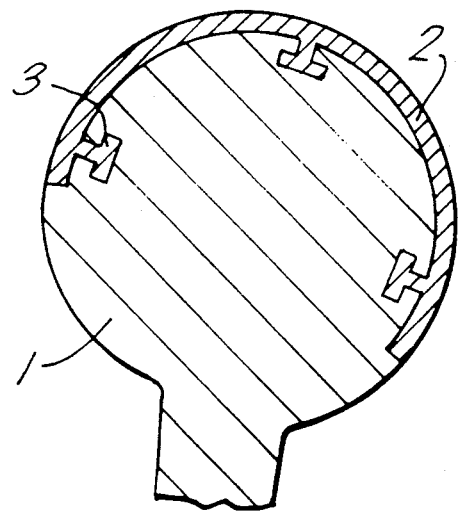
FIG. 2 is a sectional view of a portion of a femural head a portion of which head bears a wear-resistant coating.
Figure 3:
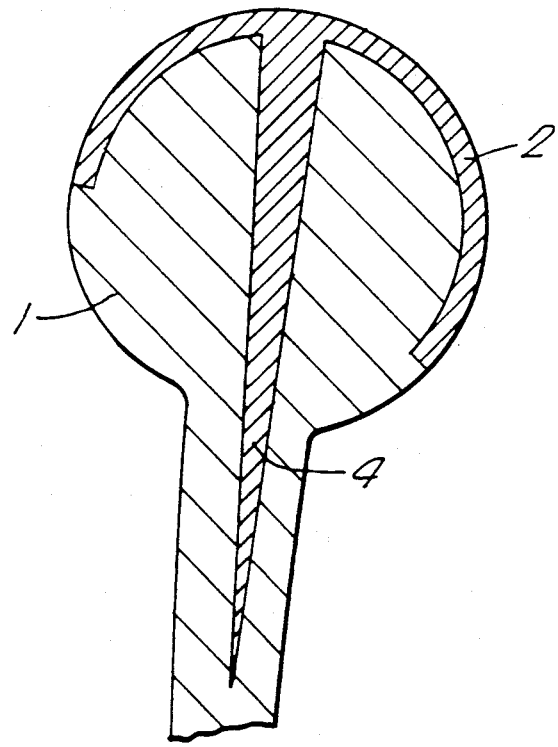
FIG. 3 is a sectional view of a portion of a further femural head bearing a wear-resistant coating.

In FIGS. 2 and 3, the same numbers as in FIG. 1 are used to indicate the same components. In FIG. 2, the metal coating 2 covers only a portion of the head. In FIG. 3, the metal coating is provided with an extension 4. On curing Composition A, the extension 4 becomes trapped in the head.

Preparation of Composition A and a prosthetic device according to the present invention may be effected by processes well known in the art. For example, Component A and the filler may be mixed by known techniques e.g. rolling, calendering or milling, e.g. Z-blade mixing. Alternatively, but not preferred, they may be mixed in the mould (for the prosthetic device) in which they are to be cured. We do not exclude the possibility that the mixture of Components A and B may be diluted with a low-boiling solvent in order to provide Composition A of the desired fluidity, the low boiling solvent being caused or allowed to evaporate before the composition is cured. However, this possibility is not preferred.

According to a yet further aspect of the present invention there is provided a process for the preparation of a prosthetic device which process comprises the steps of:

(a) charging a mould of appropriate size and shape with Composition A; and
(b) curing Composition A in the presence of a suitable catalyst under appropriate conditions.

Curing may be effected by techniques well known in the art, e.g. a peroxide cure using a suitable peroxide. Preferably curing is effected at an elevated temperature and pressure, e.g. about 80° C., using a peroxide having a suitable half-life at that temperature, e.g. t-butyl per-2-ethyl hexanoate. Such a curing technique has the advantage that the viscosity of the polymerisable composition is lowered (hence it flows more readily) and/or mould times are reduced and the properties of the cured product are improved as a result, it is believed, of a higher degree of cure.

However, where the polymerisable composition is transparent or translucent we do not exclude the possibility that the curing thereof may be initiated by a light curing catalyst, e.g. as described in our UK Patent Specifications Nos. 1,408,265 and 1,494,903 or our European Patent Specification Nos 0,059,649 and 0,090,493. The present invention is further illustrated by reference to the following Examples.

Water Test

"Water extractibles" and "water uptake" were determined by the following procedure.

A moulded sheet (0.3 cm × 3 cm × 1 cm) (Weight A) of the composite was immersed in water at 74° C. until it reached constant weight (typically after more than 400 hrs) (Weight B). The moulded sheet was then dried under vacuum at 40° C. until it reached constant weight (Weight C). The above parameters were then calculated from the equations:

$$\text{Water uptake} = \frac{B - A}{A} \times 100\%$$

and $$\text{Water extractibles} = \frac{A - C}{A} \times 100\%$$

Example 1

This Example illustrates a composition according to the present invention and a composite prepared therefrom.

A portion (100 gms) of the dimethacrylate of oxyethylated bis-phenol A (Diacryl 101, RTM), cyclohexyl methacrylate (100 gms), p-methoxy-phenol (0.14 gms) and t-butyl per-2-ethylhexanoate (1.0 gms) were mixed at room temperature (Mixture A). A silane coupling agent (A174 ex U.C.C.; 1.4 gms), n-dodecylamine (0.7 gms), and di-2-ethyl-hexyl phosphate (0.8 gms) were added to a portion (100 gms) of Mixture A which was then stirred for 20 mins at room temperature (Mixture B). Silica powder (Aerosil OX50 (RTM); 60.30 gms) was added to a portion (100 gms) of Mixture B and stirred until a uniform dispersion was obtained.

Powder of a barium borosilicate glass (Raysorb T3000 (RTM)), was added to the dispersion until a viscous mixture was obtained; stirring became difficult. The viscous mixture was stirred with a mechanical Z-blender and stirring was continued with the addition of further amounts of the glass powder; the total amount of glass powder added was 532 gms. Stirring was continued for 5 minutes and then for a further 2 minutes under a vacuum of 26 (ins of Hg) to afford a composition according to the present invention. It was a white, slightly tacky semi-solid which was found by pyrolysis to have an ash content of 86 wt %, ie the inorganic particles provided less than 80% by volume.

A sheet (thickness 3mm) was prepared by compression moulding a sample (70 gms) of the composition under the following cycle:
80° C./5 tons gauge/30 mins; and
110° C./5 tons gauge/30 mins A strong, stiff moulding was obtained and the curing thereof was completed by heating at 150° C. for 30 minutes in a fanned oven. The product from the oven (Product A) was found to have a flexural modulus of 19.7 GPa and a flexural strength of 128 MPa. Samples of Product A were immersed in distilled water at 74° C.

until they were saturated; they had an average water uptake of 0.24%. Exhaustive drying of these samples indicated that 0.1% had been extracted during the immersion.

Samples of Product A were steam auto-claved at 121° C. for 25 minutes. The samples recovered therefrom showed no visual change and Dynamic Mechanical Analysis curves of modulus and loss process revealed that they were unchanged.

Further samples of Product A were conditioned at 37° C. in distilled water or in phosphate-buffered saline. Discrete samples were removed periodically and their compressive strength and fracture toughness ($K_{1C}$, by the method of Pillar, Vowles and Williams, (J. Biomedical Materials Research, 1989, 21, 145) were determined. The results are shown in Table 1 from which it can be seen that such treatment produces minimal change in these properties.

A sample of the semi-solid was compression moulded under the conditions described in Example 1. The product (Product B) was found to have a flexural modulus of 27.0 GPa and a flexural strength of 131.6 MPa at room temperature.

Samples of Product B were examined as described in Example 1 and were found:

(a) to be unchanged, visually and as indicated by DMA's, after autoclaving; and
(b) after equilibrating in distilled water at 74° C., to have a water uptake of 0.25% w/w and a flexural modulus of 27.3 GPa and a flexural strength of 112.9 MPa (at room temperature).

The compressive strength and fracture toughness ($K_{1C}$) of Product B after immersion in certain liquids was determined under the conditions described in Example 1. The results are shown in Table 2 from which it can be seen that such treatment effects little or no change in these properties.

TABLE 1

| Period of immersion | Distilled water | | Phosphate-buffered saline | |
|---|---|---|---|---|
| | $K_{1C}$ (MN$^{-3/2}$) | Comp Strength (MPa) | $K_{1C}$ (MN$^{-3/2}$) | Comp Strength (MPa) |
| 0 (Dry) | 1.31 (±0.24) | 170 (±34) | ND | ND |
| 24 hours | 1.20 (±0.09) | 215 (±40) | 1.18 (±0.13) | 232 (±22) |
| 7 days | 1.06 (±0.07) | 206 (±26) | 1.13 (±0.07) | 185 (±27) |
| 14 days | ND | 240 (±30) | ND | 236 (±17) |
| 1 month | 1.26 (±0.12) | 211 (±29) | ND | 222 (±23) |
| 3 months | 1.04 (±0.07) | 237 (±24) | 1.06 (±0.09) | 208 (±39) |
| 6 months | 1.03 (±0.06) | 208 (±39) | 1.16 (±0.21) | 218 (±31) |

ND: Not determined

TABLE 2

| Period of immersion | Distilled water | | Phosphate-buffered saline | |
|---|---|---|---|---|
| | $K_{1C}$ (MN$^{-3/2}$) | Comp Strength (MPa) | $K_{1C}$ (MN$^{-3/2}$) | Comp Strength (MPa) |
| 0 (Dry) | 1.47 (±0.16) | 185 (±47) | ND | ND |
| 24 hours | 1.33 (±0.15) | 204 (±28) | 1.33 (±0.17) | 199 (±47) |
| 7 days | 1.30 (±0.13) | 204 (±29) | 1.33 (±0.17) | 200 (±26) |
| 14 days | ND | 239 (±28) | ND | 231 (±34) |
| 1 month | 1.29 (±0.11) | 246 (±22) | 1.26 (±0.11) | 173 (±36) |
| 3 months | 1.29 (±0.14) | 222 (±23) | 1.26 (±0.11) | 215 (±29) |
| 6 months | 1.26 (±0.07) | 231 (±25) | 1.27 (±0.08) | 223 (±39) |

ND: Not determined

Example 2

This Example illustrates a further composition according to the present invention and a composite prepared therefrom.

An "aromatic-methacrylate" oligomer (190 gms; prepared as in Example 14 of our European Patent Specification No 0,112,650), penta-fluorostyrene (63 gms), p-methoxy phenol (0.13 gms) and t-butyl-per-2-ethyl hexanoate were stirred at room temperature for 20 minutes and then at a vacuum of (30 ins Hg) for 30 minutes. A portion (100 gms) of that mixture, silane coupling agent (A174; 1.4 gms), dodecylamine (0.7 gms), and di(2-ethyl hexyl) phosphate (0.8 gms) were stirred for 5 minutes at room temperature.

As described in Example 1, silica (OX50; 63 gms) and then Raysorb T3000 (RTM; 543 gms) were added to the mixture. The product obtained (Composition A) was an off-white tack-free semi-solid and was found to have an ash-content of 87.5% w/w, ie the inorganic particles provided less than 80% by volume.

Example 3

This example illustrates a further composition according to the present invention and a composite prepared therefrom.

First Stage

A portion of dimethacrylate of oxyethylated bisphenol A (Diacryl 101, RTM; 25 gms), cyclohexyl methacrylate (25 gms), 4-methoxy phenol (0.025 gms) and t-butyl per-2-ethyl hexanoate (0.25 gms) were mixed at room temperature (Mixture A). A silane coupling agent (A174; 0.35 gms), m-dodecylamine (0.18 gms) and di-2-ethylhexyl phosphate (0.2 gms) were added to a 5 minutes at room temperature (Mixture B). Silica powder (Aerosil OX50 (RTM)- 15.1 gms) was added to a portion (25 gms) of Mixture B and stirred until a uniform dispersion was obtained.

Second Stage

A portion (115 gms) of a strontium containing glass powder (Raysorb T4000 (RTM)) was added to the dispersion until stirring by hand became difficult. Mixing of the viscous mixture was continued on a mechanical twin-roll mill, with the successive addition of 5 portions of 2 gms of T4000, each portion being mixed for 2 minutes. The total amount of T4000 powder added was thus 125 gms. Stirring was continued for 30 minutes and then for a further 10 minutes under a vacuum of >28 (ins of Hg) to afford a composition according to the present invention.

6 rectangular samples (2.8×8.8×50 mm) were prepared by compression moulding of the composition under the following cycle:
100° C./5 tons gauge/30 minutes;
150° C./air/30 minutes (post cure).

The product was found to have an average flexural modulus of 18.3 GPa and an average flexural strength of 74.5 MPa.

Examples 4 and 5

These Examples illustrate further compositions according to the present invention, and composites prepared therefrom.

The procedure of the First Stage of Example 3 was repeated except that the dimethacrylate of oxypropylated bisphenol A (50 gms) was used instead of the mixture of the dimethacrylate of oxy-ethylated bisphenol A (25 gms) and cyclohexyl methacrylate (25 gms).

Powder of Raysorb T4000 (RTM) (45 gms) was added to the dispersion until manual stirring became very difficult. Mixing was continued on a mechanical twin-roll mill with the addition of further amounts of the powder (30 gms for Example 4, 57 gms for Example 5) the total amounts of T4000 added being thus respectively 75 and 102 gms. Stirring was continued for respectively 30 minutes and 2 hours for the two composites, and then for a further 10 minutes under a vacuum of >28 (ins of Hg).

6 rectangular samples of both Examples were compression moulded under the conditions described in Example 3.

The products were found to have an average flexural modulus of 13.7 GPa (Example 4) and 16.2 GPa (Example 5) and an average flexural strength of respectively 83.6 and 68.5 MPa. This illustrates the affect of concentration of a certain particulate inorganic solid on flexural modulus.

I claim:

1. A prosthetic device comprising a composite wherein the composite has a flexural modulus in the range of values recorded for compact bone and is preparable by curing a curable composition which comprises an intimate mixture of
   Component A: an addition polymerisable composition;
   Component B: at least one particulate inorganic solid which provides up to about 80% by volume of the composite;
   Component C: a stabilising or dispersing agent; and
   Component D: a high temperature peroxide.

2. A device as claimed in claim 1 wherein the product obtained on curing of Component A per se has a flexural modulus of about 3 GPa.

3. A prosthetic device as claimed in claim 1 wherein the composite has water extractibles of less than 0.15% and a water uptake of less than 0.3%.

4. A prosthetic device as claimed in claim 1 wherein Component A comprises a substance bearing a plurality of addition-polymerisable olefinically unsaturated carbon-carbon double bonds per molecule.

5. A prosthetic device as claimed in claim 4 wherein the said plurality of which Component A is comprised are present in an oligomer.

6. A prosthetic device as claimed in claim 5 wherein Component A further comprises a monomer bearing one carbon-carbon addition-polymerisable double bond.

7. A prosthetic device as claimed in claim 6 wherein the said monomer is a cyclo-hexyl methacrylate.

8. A prosthetic device as claimed in claim 4 wherein the said substance comprises a di-(alk)acrylate of an ethoxylated bis-phenol-A.

9. A prosthetic device as claimed in claim 8 wherein the said di-(alk)acrylate is a di-methacrylate.

10. A prosthetic device as claimed in claim 1 wherein the particulate inorganic solid is a glass.

11. A prosthetic device as claimed in claim 1 wherein the particulate inorganic solid provides between 65 and 70% by volume of the composite.

12. A prosthetic device as claimed in claim 1 wherein a portion of the particles are sub-micron particles.

13. A device as defined in claim 1 wherein the composite flexural modulus is between 15 and 30 GPa.

14. A prosthetic device as claimed in claim 1 or 13 in the form of a bone-joint replacement.

15. A bone-joint replacement as claimed in claim 14 wherein the composite provides substantially all of the cross-section of the stem of a replacement disposed in the intramedullary canal of a long bone such that the similarity of the flexural moduli of the composite and cortical bone in the said long bone alleviates the problems associated with the loosening of bone-joint replacements.

16. A bone-joint replacement as claimed in claim 15 in the form of a femoral head.

17. A femoral head as claimed in claim 16 wherein at least a portion of the wear surface of the femoral head s coated with a wear-resistant coating.

18. A prosthetic device as claimed in claim 1 wherein the composite is steam-sterilisable.

19. A prosthetic device prepared by
   (a) charging a curable composition as defined in claim 1 to a mould of appropriate size and shape;
   (b) applying a vacuum thereto to substantially de-gas and remove entrapped air therefrom; and
   (c) curing the curable composition at elevated temperature and pressure in the mould.

20. A sterilised prosthetic device prepared by steam-sterilizing the prosthetic device claimed in claim 18 or 19.

* * * * *